United States Patent [19]

Libby

[11] Patent Number: 4,500,515

[45] Date of Patent: Feb. 19, 1985

[54] METHOD FOR TREATING ALCOHOL AND DRUG ADDICTS

[76] Inventor: Alfred F. Libby, P.O. Box 4179, San Clemente, Calif. 92672

[21] Appl. No.: 479,713

[22] Filed: Mar. 28, 1983

Related U.S. Application Data

[63] Continuation of Ser. No. 253,712, Apr. 13, 1981, abandoned.

[51] Int. Cl.³ .................. A61U 31/365; A61K 33/06; A01N 43/78
[52] U.S. Cl. .................................. 424/154; 514/474; 514/276
[58] Field of Search .................. 424/10, 154, 255, 280

[56] References Cited

U.S. PATENT DOCUMENTS

| | | | |
|---|---|---|---|
| 3,989,823 | 11/1976 | DiCostanzo | 424/280 |
| 4,167,562 | 9/1979 | Evesr | 424/280 |
| 4,322,407 | 3/1982 | Ko | 424/280 |

OTHER PUBLICATIONS

Scher et al., J. Orthomolecular Psychiatry, vol. 5, No. 3, (1976) pp. 195–198.

Free and Sanders, J. Orthomolecular Psychiatry, vol. 7, No. 4, (1978), pp. 264–270.

Kalokerinos and Dettman, Escape from Hell, Now Horizons, vol. 5, No. 2, Apr. 1979, pp. 5–12.

Libbey and Stone, Australasian Nurses, J. vol. 7, No. 6, (1978) pp. 3–13.

Stone, *The Healing Factor*, "Vitamin C against Disease " (1972) pp. 157–158.

Zannoni et al. Trends in Biochemical Sciences, 1 (6) 1976, pp. 126–128.

*Primary Examiner*—Stanley J. Friedman
*Attorney, Agent, or Firm*—Peter J. Groom

[57] ABSTRACT

A therapeutic composition for detoxifying drug or alcohol addicts comprises sodium ascorbate, calcium gluconate, magnesium chloride, and thiamine hydrochloride in a saline solution compatible with blood serum.

A method for detoxifying addicts begins with oral doses of sodium ascorbate, calcium and magnesium for about 6 hours, after which time the therapeutic detoxifying composition is parenterally administered to complete detoxification in the absence of withdrawal symptoms and "guts craving". Amino acids, vitamins, minerals, and proteins are given after detoxification to replenish the body's supply of these essential items.

13 Claims, No Drawings

METHOD FOR TREATING ALCOHOL AND DRUG ADDICTS

This is a continuation of Ser. No. 253,712 filed Apr. 13, 1981, now abandoned.

FIELD OF THE INVENTION

This invention pertains to a treatment regimen for drug addicts and alcoholics. More particularly, it provides a method which totally and rapidly detoxifies the subject while inhibiting manifestation of withdrawal symptoms and eliminating the physiological/psychological "guts craving", and at the same time rebuilds the nutritional health of the patient.

BACKGROUND OF THE INVENTION

Drug addiction and alcoholism are serious social problems. Many addictive drugs are now being abused in the United States and the rest of the world at high cost to society. Vast sums of money are spent in treatment and rehabilitation programs in a futile effort to solve the problem. As illicit narcotics are expensive, it is not uncommon for an addict to engage in criminal enterprises, such as robbery or theft, to obtain the money necessary to support his or her drug habits.

Current approaches to heroin addiction include methodone maintenance programs where a government sponsored narcotic, methodone, is substituted for the illegal narcotic, heroin. This method is self-defeating because methodone is itself addicting and one form of drug addiction is merely substituted for another. In fact, this method does not free the patient from drug addiction.

Another approach to heroin addiction is a simple withdrawal program, otherwise known as "cold turkey", where the addict is physically prevented from ingesting the addicting drug, i.e., jail. Consequently the addict goes through a withdrawal period marked by severe muscle spasms, chills, lacramation, diarrhea, vomiting, and a continuing "guts craving" for the narcotic. The "cold turkey" method involves a not inconsiderable amount of pain and for this reason is dreaded and avoided by addicts.

Another method of withdrawal from addicting drugs is the methadone detox method. A progressively reduced dose of methadone is given until a zero dose is reached at the twenty-first day. The addicted patient comes away "sick" and still has the "guts craving" for drugs, hence the patient returns to drug usage to "get well" from the methadone detox.

An additional method of drug detox is the use of valium, darvon, darvon-n, etc. to symptomatically assist the individual off the offending drug. This technique is also unsatisfactory.

Alcoholism is another serious and costly social problem. Aside from the expense of treating severe cases of alcoholism, the social cost in terms of lost productivity, and benefits paid to families of alcoholics in the form of disability insurance, are considerable. Current approaches to alcoholism include a method of alcohol loading to induce sickness, after which unpleasant confrontations are initiated to stimulate aversion to drinking.

There is also the electrode method of stimulus-response to create aversion. An alcoholic is given a drink and as the drink is raised to the lips he or she receives an uncomfortable electric stimulus.

There is also the supportive A-A concept of "cold turkey" detox which encourages the alcoholic to admit he or she has hit bottom as an alcoholic in order to induce a desire to get well.

All the above approaches, and others known to date, treat alcoholism or drug addiction as a problem essentially confined to preventing ingestion of the offending substance. All require anywhere from 72 hours to 21 days to accomplish detoxification, which, with withdrawal symptoms, is a slow and painful process. None do anything to reduce either withdrawal symptoms or the "guts craving" for the narcotizing substance. Slight, if any, attention is directed toward the patient's nutritional health or lack thereof. Once the patient is released from the cocoon environment of these programs, he or she alone must cope with the stress of everyday life and not infrequently returns to the drug environment.

There is need for a method for rapidly detoxifying drug or alcohol addicts, which both blocks withdrawal symptoms and eliminates the "guts craving" effect. The need extends to a regimen which provides the subject with adequate tools for handling the stress of everyday life.

SUMMARY OF THE INVENTION

In accordance with the described needs, there is provided both a therapeutic detoxifying composition and method for treating alcoholics and drug addicts, and those dependent on a toxic substance, which addresses substance abuse as a metabolic problem. In its most complete aspects, the method addresses both detoxification and rehabilitation.

The invention provides a method for detoxifying a person from a drug or alcohol dependence. Such method comprises intravenously infusing an effective amount of a composition for limiting withdrawal symptoms during detoxification from such alcohol or drug dependence, the composition comprising the following per 1000 ml; from about 10 g to about 15 g sodium ascorbate, from about 400 mg to about 800 mg calcium gluconate, from about 200 mg to about 400 mg magnesium chloride, and from about 500 mg to about 1000 mg thiamine hydrochloride.

The composition comprises sodium ascorbate, magnesium chloride, calcium gluconate, and thiamine hydrochloride in a saline solution, all in specified proportions. The composition is endowed with polydetoxifying properties, and is effective for detoxifying a patient while blocking withdrawal symptoms and "guts craving".

The new detoxification method utilizes the therapeutic composition for substantially detoxifying a human in about 8 to 20 hours. First, ingestion of offending substances is interrupted and cut-off. The patient is then administered sodium ascorbate, preferably orally, in divided doses of about 4 to about 8 grams every two hours, for six hours unless the patient first experiences diarrhea, in which case the sodium ascorbate doses are discontinued. Concurrently with the administration of sodium ascorbate, preferably there are administered sufficient calcium for inhibiting muscle cramping and spasm, and sufficient magnesium for maintaining that calcium which is excretable from the subject in non-insoluble species. Preferably sufficient Vitamin B-1 is administered for controlling symptoms of neuritis, supplemented by a sublingually administered Vitamin B-12 lozenge booster.

About six hours after starting treatment, the method further comprises parenterally administering a sufficient volume of the therapeutic detoxifying composition for blocking withdrawal symptoms while rapidly accomplishing substantially complete detoxification. Depending on individual biochemistry, detoxification is accomplished preferably within a period of 8 to 12 hours after start of treatment for most problem substances.

The following day, rehabilitation begins with sodium ascorbate, calcium and magnesium given in one or two divided dosages in the same concentrations as before, but discontinued if diarrhea develops. Preferably 2000 mg Vitamin B1 and three sublingual Vitamin B12 lozenge are also given daily.

Rehabilitation of healthy metabolism for all substance abusers is intensified at this time with selected dosages of zinc, pantothenic acid, and amino acids supplemented with Vitamins A and B-6. The zinc and pantothenic acid is continued through return of appetite to aid recharging of adrenals. Multi-mineral and multi-vitamin formulas are thereafter administered for the remainder of the treatment, which usually lasts about two weeks.

For alcohol treatment, the treatment is the same as with drugs, except that additional substances are given after detoxification. These are a lipotrates formula, supplemented with digestive and pancreatic enzymes, glutamine, N,N dimethylglycine, lecithin, and three sublingual B-12 lozenges daily.

The patient is preferably given a series of metabolic tests before and during the treatment and is cared for on an outpatient basis thereafter, with dietary supplementation as necessary tailored for individual metabolic needs.

DETAILED DESCRIPTION

This invention provides a therapeutic detoxifying composition and treatment method for alcoholics and drug addicts, and those dependent on or exposed to a narcotizing or toxic substance, which rapidly detoxifies the subject while blocking withdrawal symptoms and the "guts craving" effect.

As used herein, "narcotic" or "narcotising substance" is used interchangeably with "offending substance" or "toxic substance," and is used to mean any of the substances which are abused, or cause a physical or psychological dependence, or to which the patient has been exposed, and is the problem substance for which the patient is referred for treatment. Examples of narcotising substances which are capable of treatment by this invention include, but are not limited to, alcohol, heroin, opium, methodone, cocaine, marijuana, LSD, PCP (so-called "Angel Dust"), barbiturates, tobacco, hashish, ganja, mescaline, Agent Orange and other illicit or prescription drugs or medications, or toxic chemicals. Presently, it appears that this invention is capable of detoxifying any substance within a 24-hour period.

The compositions of the present invention endowed with polydetoxifying properties, especially with regard to alcohol or drugs, comprise sodium ascorbate, calcium gluconate, magnesium chloride, and thiamine hydrochloride in a normal saline solution.

The saline solution is preferably a 0.9% normal solution of sodium chloride. Sodium chloride keeps electrolyte levels of the red blood cells in balance. Its normality is selected to be compatible with blood serum, so that, if injected, the solution will not appreciably alter the osmolarity of blood serum or cause homolysis of red blood cells. The saline solution irrigates the circulatory system and guards against dehydration if diarrhea develops.

Present in the saline solution is at least 10 grams, and preferably about 12.5 grams, of sodium ascorbate.

Sodium ascorbate is beneficial both for its strong detoxifying powers and its blocking powers which strongly attenuate withdrawal symptoms, and for clearing up Vitamin C deficiencies, which, when pronounced, cause disorders such as bleeding gums, inadequate collagen formation, poor wound healing, inadequate stress mechanism, and insufficient hormonal manufacture. Sodium ascorbate is preferred over other salts of ascorbic acid because sodium is an antagonist to morphine molecules and buffers ascorbate to a pH which is compatible with the circulatory system.

The term "withdrawal symptoms" as used herein is intended to include those symptoms known to those skilled in the art attendant upon forced discontinuation of ingestion of a narcotic substance, and includes vomiting, severe muscle spasms, agitation, lacramation from the nose and eyes, uncontrollable urination, nausea, and, in severe cases, convulsions, respiratory failure, and cardiac arrest. This type of symptomology is, for example, observable during the "cold turkey" withdrawal method of treating either drug or alcohol addiction.

Calcium gluconate addresses calcium deficiency, controls muscle spasm and cramping, and nourishes nerves, muscle, and bones. It enhances absorption of sodium ascorbate. Calcium gluconate is presently preferred over other salts of calcium because it causes minimal irritation to the system when injected. Calcium gluconate is present in a preferred dosage of about 200 mg. to about 400 mg. in a 1000 cc volume of the saline solution.

Magnesium chloride has a calming effect on the patient. It also has anti-convulsive properties, regulates blood pressure and enhances absorption of the calcium ion. The magnesium present also maintains the calcium ion in soluble form and thus aids in the prevention of formation of calcium oxalate crystals in the urinary tract. From about 400 mg to about 800 mg magnesium chloride is preferably present in 1000 cc of the saline solution.

Thiamine hydrochloride nourishes the nervous system by promoting better nerve transmission, and controls symptoms of neuritis, such as agitation, nervousness, burning soles of feet, shaky hands, shaky fingers, and quivers, and, for alcoholics, symptoms of delirium tremens. This ingredient is present in a preferred dosage of about 500–1000 mg in a 1000 cc saline solution, although up to 10 g can be present if needed to control shakiness of the patient.

The ingredients of the composition are available commercially in the correct proportions for a 1000 cc composition as solutions contained in 5 or 10 cc sterile vials without preservatives. To an approximately 900–950 cc volume of the saline solution are added the ingredients, and sufficient saline solution is then added to reach a 1000 cc volume, which is then ready for administration to the patient. While the preferred concentration ranges of the ingredients have been given with respect to a 1000 cc volume of solution, it will be appreciated by those skilled in the art that lesser or greater volumes can be prepared with the ingredients present in equivalent concentrations.

The composition is preferably administered parenterally at a rate such that 1000 cc are "run" into the patient in about 2 to about 4 hours. The rate can be speeded up if necessary, to control withdrawal symptoms, muscle cramping or spasm, or shakiness.

Below, non-limiting examples are given of formulas for the composition of this invention.

Formula No. 1—Parenteral Solution

Sodium ascorbate 12.5 mg
Calcium gluconate 400 mg
Magnesium Chloride 800 mg
Thiamine Hydrochloride 1000 mg
0.9% normal NaCl 1000 cc Formula No. 2—Parenteral Solution Sodium ascorbate 12.5 g
Calcium gluconate 200 mg
Magnesium Chloride 400 mg
Thiamine Hydrochloride 500 mg
0.9% normal NaCl 1000 cc The solution can be given either intravenously (IV) or intramuscularly (IM) but IV is presently preferred. The patient can be started on a 1000 cc dosage and given additional 1000 cc or smaller volumes as needed to effect detoxification while preventing dehydration and blocking withdrawal symptoms and neuritis.

The novel injectible solution has versatile utility in that, when given in sufficient volumes, it is effective for essentially complete chemical detoxification of any toxic substance within about 4 to 24 hours after initial injection. These include, for example, alcohol, heroin, opium, methodone, cocaine, marijuana, LSD, PCP, barbiturates, hashish, ganja, mescaline, and Agent-Orange.

The therapeutic detoxifying composition has presently preferred utility in a new method for treating alcohol and drug addicts, and those exposed to toxic substances, according to this invention, as explained below.

Before initiating treatment, the patient is preferably placed in a controlled environment so that the program may be properly monitered administered. To start the treatment, ingestion of the offending substance, be it alcohol, drugs, or tobacco, is interrupted and made unavailable to the subject.

The patient is given an initial dose of sodium ascorbate, preferably with calcium, magnesium, Vitamin B1, and Vitamin B12. The sodium ascorbate present in this dosage begins to create a blocking dose for preventing withdrawal symptoms and for detoxifying the patient. The first dose contains from about 4 to about 8 grams sodium ascorbate, preferably about 7 grams.

It is preferable to give the initial dosage orally as it is simpler than injection and, for drug addicts, does not reinforce memories of needle habits. Moreover, substance addicts generally have constipated bowels. Oral sodium ascorbate cannot bypass the gastrointestinal tract and hence induces return to normal peristaltic habits. This helps clear toxins from the system as detoxification progresses.

For reasons more fully explained below, detoxification is rapid after the sixth hour when the therapeutic detoxifying composition is administered. However, as the alcohol or drug addiction problem is metabolic, nutritional deficiencies play a role once detoxification is complete. One indicium of such deficiency is abnormal psychology. Hence, it is desirable to obtain a psychological profile before detoxification reaches this point in order to have a baseline psyhcological evaluation for use in subsequent evaluation during rehabilitation. Initial oral doses of sodium ascorbate start detoxification at a rate which is not too rapid for permitting observation for several hours so that the baseline profile may be obtained before psychological symptomology varies with rapid detoxification.

Additional sodium ascorbate doses are given every two hours, including the sixth hour, unless diarrhea occurs first, in which event no further doses are given. Each sodium ascorbate dose is from about 4 to about 8 grams, preferably about 5 grams.

The particular dosage of sodium ascorbate needed for inducing diarrhea represents a saturation level in the body and is variable due to biochemical individuality of the patient, the extent of toxicity present, the particular substance(s) causing the problem, their combinations, if any, and the length of exposure to them. Generally the deeper that toxins are stored in tissue, the more sodium ascorbate will be needed for inducing diarrhea. For example, alcohol is not stored in tissue except for the liver, and diarrhea usually occurs in alcoholics before the first four doses of sodium ascorbate can be given. On the other hand, methadone involves two toxic substances and diarrhea seldom occurs before the thirtieth hour.

I have discovered that about 28 to about 35 grams sodium ascorbate given the first day according to principles of this invention is a critical blocking dose generally effective for complete detoxification essentially in the absence of withdrawal symptoms.

Doses of sodium ascorbate above about 35 grams can be given but appear to give no additional benefits for most cases of toxicity. Doses below about 28 grams are not as effective as a full blocking dose in attenuating withdrawal symptoms and for accomplishing rapid and essentially complete detoxification during a period of about 8 or 10 hours after start of treatment.

It is not known how sodium ascorbate exerts its blocking powers. Nevertheless, I have discovered that about 30 to 32 grams sodium ascorbate given orally in a 24-hour period, is generally effective for blocking all symptoms of withdrawal during a process of detoxification, even if detoxification does not progress to completion. However, although the patient will not experience withdrawal symptoms per se, nutritional deficiencies may become manifest, as explained below.

An oral dose of 28 to 35 grams sodium ascorbate is usually effective for detoxifying most patients, and, for these individuals, represents a saturation level in the body. When the blocking dose is given both orally and parenterally, according to principles of this invention, about 28 to about 35 grams sodium ascorbate is generally sufficient to cause chemically complete detoxification within about 12 hours, although more is infrequently needed if toxicity levels are unusually pronounced.

In the presently preferred practice of this invention, initially three or four doses of sodium ascorbate are given orally every two hours, which builds up about 15 to about 25, preferably either about 17 or 22, grams toward the blocking dose. If diarrhea occurs, then the oral doses are discontinued.

Six hours into the treatment, whether or not diarrhea has occurred, the patient is given a parenteral dosage of the detoxifying composition, which contains at least 10 grams, and preferably about 12.5 grams, sodium ascorbate in liquid form without preservatives, which is preferably dispersed in 1000 cc of 0.9% normal saline solution. The combination of oral initial doses sodium ascorbate with the parenteral dose contained in the composition of this invention achieves the usual blocking dose level of about 28 to 35 grams sodium ascorbate.

It is presently preferred that the parenteral dose take about two to four hours to run, which rapidly detoxifies the patient while blocking withdrawal symptoms. At the end of the run, chemical detoxification is essentially complete, for most substances treated. At this point the patient is detoxified chemically and will not exhibit withdrawal symptoms.

While the initial oral doses of sodium ascorbate help cause the bowels to deconstipate, the parenteral dose is available immediately in the system without having first to pass through the digestive barrier. Detoxification speeds up enormously and occurs in the absence of withdrawal symptoms.

Parenteral administration of sodium ascorbate, preferably from the composition of this invention described previously, is beneficial because addicts of alcohol and many drugs are afflicted with malabsorption in the intestinal tract and would not readily absorb a one-time oral dose of at least 10 grams sodium ascorbate.

The treatment is tailored to individual biochemistry. Thus, up to four oral doses of sodium ascorbate are given, depending on whether diarrhea occurs. If diarrhea occurs, oral doses are stopped so as not to induce further diarrhea, for extensive diarrhea before the parenteral solution is given could dehydrate the patient.

It is desirable that the patient develop at least one episode of diarrhea, for this indicates that sodium ascorbate has reached a saturation level in the individual and that detoxification is occurring. If diarrhea does not occur during the initial six hours, in most cases it will develop during the run of the parenteral solution. In that event, since detoxification is complete, further oral sodium ascorbate is thereafter given for rehabilitative purposes and is not restarted until the following day and after the patient has had at least one firm stool.

However, diarrhea sometimes does not occur even after one full 1000 cc preferred parenteral dose containing sodium ascorbate has been given, either because toxicity is acute or the bowels are exceptionally constipated. If the cause is toxicity, the patient may start withdrawal symptoms after the IV has run since detoxification is not yet complete. The patient is then restarted on sodium ascorbate, either orally or parenterally, as needed to control perceived withdrawal symptoms. Whether sodium ascorbate is given orally or parenterally depends on the strength of the symptoms, which is a function of toxicity and individual biochemistry and can only be determined by clinical observation.

The patient is restarted on additional doses of sodium ascorbate, generally about 4 to about 8 grams every 2 hours for oral doses, or at least 10 grams for the IV, to reach a saturation point which will stimulate the bowels to move. Once the bowels move, they are refunctioning, and cumulative toxins are removed, and, along with it, the "guts craving", which never returns thereafter. Since detoxification has now occurred, the patient is not given additional sodium ascorbate until the following day, when it is restarted on a reduced basis of about 6 to about 8 grams per day, for rebuilding ascorbate levels in the body and addressing long-term deficiencies.

If the patient is detoxified but has exceptionally constipated bowels, he or she may resist diarrhea but not exhibit withdrawal symptoms, and is permitted to rest until the following day. The second day, oral doses of sodium ascorbate are restarted in divided doses as before but continue as necessary up to a "full" blocking dose of about 32 grams in order to stimulate diarrhea. In exceptional cases, where diarrhea still has not occurred, commencing the third day, preferably the patient is started on additional 1000 cc parenteral doses of the therapeutic detoxifying composition, each containing about 10 to about 15 grams sodium ascorbate, and additional oral doses of sodium ascorbate, as needed for causing one episode of diarrhea, which soon occurs.

The treatment is tailored to the degree of toxicity which is a function of biochemical individuality. Although a one time dose of between about 28 and about 35 grams sodium ascorbate, given orally and parenterally, is sufficient in most cases to effect complete detoxification, occasional cases are unique in requiring more sodium ascorbate to reach a saturation level in the body. This can only be determined on a clinical basis by observing the appearance or absence of withdrawal symptoms and diarrhea.

Generally the parenteral solution, containing 1000 cc of the detoxifying composition, is run to completion in about two to about four hours. If at any time the patient begins to develop withdrawal symptoms, the solution is made to run faster to control the symptoms. If the solution has run completely and withdrawal symptoms appear, then detoxification is not yet complete, and additional parenteral solutions are run as needed to control the symptoms and complete detoxification. In usual cases involving alcohol or drugs, only one 1000 cc parenteral solution containing about 12.5 grams sodium ascorbate suffices for complete detoxification after the initial oral doses; however, due to biochemical individuality and differences in toxic exposure, additional parenteral doses are at times required.

The mechanism of detoxification is not perfectly understood. Generally, once ingested, toxins are not excreted by the body but are stored in various tissue and sometimes take years for removal by natural mechanisms. For drug abuse in particular, it is believed that narcotic molecules associate with opiate receptor sites, particularly in the limbic section of the brain, the gastrointestinal tract, the spinal cord, and other tissue, and disrupt the body's pain killing mechanism, involving production of substances identified as endorphins and enkephalons. For alcoholism, ethanol destroys tissue, especially through fatty infiltration of the liver and by causing malabsorption of nutirents from the gastrointestinal tract, and distortion of pancreatic function through destruction of digestive enzymes and insulin manufacturing capabilities of the pancreas. In either case, offending substances tend to destroy essential vitamins, amino acids and minerals, and the body's capability of using them.

Without intending to be bound by theory, sodium ascorbate appears to detoxify the receptor sites, and other body tissue, by displacing toxins, which causes them to be excreted. The detoxification properties are believed enhanced by the presence of calcium gluconate, mangesium chloride, and thiamine hydrochloride in the compositions of this invention. Sodium ascorbate may also temporarily associate with toxin storage sites in the body and prevent later reoccupation by any subsequently available toxic molecules, thereby preventing flashbacks, etc., from hallucinogenic drugs.

In place of oral sodium ascorbate, other salts of ascorbic acid, such as potassium ascorbate, can be orally given, but sodium ascorbate is presently preferred, both for the beneficial effect of the sodium portion of the molecule in the body, and for the buffering effect of sodium on sodium ascorbate, which, having a relatively mild pH of about 7.5, is readily digestible.

It is also possible to use ascorbic acid, but I have found that its relatively lower pH when given orally in dosage sizes equivalent to the initial (oral) doses of sodium ascorbate threatens severe gastrointestinal distress, which manifests as hyperbloating, ulcer formation, stomach and abdominal cramps, and vomiting. For this reason, ascorbic acid is not presently preferred.

Offending substances, such as alcohol or drugs, anesthetize the body so that deficiencies of essential proteins, amino acids, vitamins and minerals do not manifest. When detoxification progresses, the substances are no longer available to mask nutritional deficiencies, which then begin to appear. Although sodium ascorbate accomplishes rapid detoxification in the essential absence of withdrawal symptoms, several latent nutritional deficiencies will generally appear unless addressed during detoxification. The major problem areas are deficiencies of calcium, Vitamin B1, and Vitamin B12, although generally across-the-board deficiencies of essential proteins, amino acids, vitamins and minerals are present.

The deficiencies occur through a junk food diet or one devoid of nutrition, and by a destructive influence of effending substances upon the body's supply and replenishment of essential proteins, amino acids, vitamins and minerals. While substance addiction accelerates and masks deficiencies, which appear on detoxification, they are not a symptom of chemical withdrawal per se, although they may previously have been incorrectly identified as such by some workers in the art. Rather, chronic deficiencies are perceived as symptomology because detoxification has removed the masking effect of the offending substance(s). For this reason, etiology of nutritional deficiency, while not a symptom of withdrawal, will accompany detoxification unless addressed.

Thus the above-described detoxification treatment, using sodium ascorbate both orally and parenterally in the composition of this invention, has utility as a rapid detoxification technique proceeding in the essential absence of withdrawal symptoms. However, any nutritional deficiencies will be unmasked once detoxification has progressed substantially. This is a major reason why the composition described previously is presently preferred for practice of the method of this invention. The ingredients of the composition have been selected for detoxifying the patient while both blocking withdrawal symptoms and controlling major problem symptoms of nutritional deficiency. As the composition speeds up detoxification rapidly, however, if oral sodium ascorbate alone has preceded the parenteral dose of the composition, the ingredients themselves in their presently preferred concentrations may not be fully effective in controlling rapidly manifesting chronic deficiency.

Thus, as an improvement over the detoxification method described, the deficiencies are preferably addressed from the start of the treatment before the parenteral composition is given. In particular, calcium, magnesium, Vitamin B1 and Vitamin B12 are given. Concurrent with the oral doses of sodium ascorbate, sufficient calcium is administered for inhibiting muscle cramping, while sufficient magnesium is administered for maintaining, in non-insoluble species, that calcium which is excretable by the subject.

Calcium inhibits muscle cramping and spasm and is an essential mineral required for normal metabolism, being important to healthy nerves, muscles, and bones. Alcohol and drug addicts frequently eat diets poor in calcium. This threatens demineralization of bones and teeth. Administration of calcium address calcium deficiencies which would otherwise mainfest as muscle cramping and spasm. Thus, sufficient calcium is administered for controlling muscle spasm and cramping, preferably about 200 to about 800 milligrams calcium each time an initial dose (4-8 grams) of sodium ascorbate is given.

In addition to these dosages, additional sufficient calcium is administered for inhibiting muscle cramping as required. This is determined on a p.r.n. basis and requires observation of the patient. Clinically, I have found that as soon as a patient exhibits muscle cramping, an immediate additional oral dosage of about 350 to about 400 milligrams calcium is usually sufficient to block spasmodic attacks within about one minute.

The administration of any form of Vitamin C, in particular sodium ascorbate, involves increasing the body's intake of one form of ascorbic acid. Such an increase may stimulate excess bodily production of oxalic acid, which is believed labile to forming insoluble species or microscopic precipitates with calcium in the urinary system. However, by administering sufficient magnesium for maintaining, in non-insoluble species, that calcium which is excretable by the subject, the solubility of calcium present in the kidneys and the genito-urinary tract is increased so that calcium is maintained in non-insoluble species, which hinders formation of precipitates or salts with oxalic acid.

By "non-insoluble species" is meant any species or complex of calcium which is below saturation level and excludes precipitates or insoluble crystals. By "which is excretable by the subject" is intended to refer to any form or species of calcium present in either the kidneys or the urinary tract. Thus, administration of magnesium reduces, to an acceptable level, any risk of formation of kidney or gall stones, and the treatment can be used with patients having family susceptibility to the problem.

Magnesium has further advantages stemming from magnesium's role as a metabolic co-pilot with calcium. Calcium amd magnesium exhibit synergistic properties in essential bodily functions, most notably in absorption of these elements into muscle tissue. Thus, magnesium, in addition to hindering formation of calcium oxalate crystals, addresses calcium deficiencies by enhancing bodily absorption of calcium. Magnesium is not administered in its elemental state; however, salts or chelates of magnesium can be used and magnesium ascorbate is presently preferred.

I prefer to orally administer calcium and magnesium together in tablet form concurrently with the initial doses of sodium ascorbate. Thus, in the presently preferred method of treatment, every time an initial divided dosage of about 4 to 8 grams sodium ascorbate is administered, which preferably is on the order of every two hours during initial detoxification, I administer about 700 to about 800 milligrams calcium, and about 250 to about 350 milligrams magnesium.

For further enhancing bodily absorption of calcium and magnesium, I prefer to include phosphorous with each dose of calcium and magnesium. In the presently preferred practice of this invention, calcium is administered in the form of bone meal, due to the presence of micronutrients in bone meal. Phosphorous is also present in bone meal in a fixed ratio to calcium, generally about 113 milligrams phosphorous to 250 milligrams calcium.

However, other ratios of phosphorous to calcium ranging from about one part phosphorous to about two to about two and one half parts calcium can be considered equally effective. Phosphorous enhances absorption of calcium from the stomach into the circulatory system. Without adequate absorption, a significant portion of the administered calcium would be excreted from the gastrointestinal tract and be unavailable for inhibiting muscle spasms. However, as phosphorous is abundant in most foods, it may not always be necessary to supplement calcium with phosphorous to assure adequate uptake of calcium. Nevertheless, due to abysmal nutrition of many patients, it is preferable to include a phosphorous supplement for insuring maximum absorption of calcium into the body.

I have discovered that individuals dependent on a toxic substance are afflicted by depletion of essential B vitamins in the body by the time they seek professional help. This is probably due both to a lack of proper nutrition and a destructive effect of offending substances on the B vitamin complex in the body, and for Vitamin B1 levels in particular, is troublesome for both the alcoholic and for the drug abuser.

A Vitamin B1 deficiency manifests with symptoms quite similar to polyneuritis. The term "neuritis" as used herein, means a condition which is characterized by a syndrome of physical manifestations including: agitation, nervousness, burning soles of feet, shaky hands, shaky fingers, and quivers. These symptoms are recognizable by those skilled in the art as indicating a Vitamin B1 deficiency, and are not unlike symptoms of beri-beri.

The human species cannot synthesize sufficient Vitamin B12 and must supply requirements from exogenous sources. Symptoms of Vitamin B12 deficiency are recognized by those skilled in the art as including disturbed mental health, which can progress to paranoia or schizophrenia, low blood count, rapid pulse, cardiac pain, poor digestion, lack of appetite, neuritis, optic atrophy, diarrhea, loss of weight, and tongue inflammation.

Other B Vitamin deficiencies causes symptomology, in particular, for Vitamin B3, symptoms of pellagra run a parallel course to schizophrenia.

Vitamin B1 dosages are preferably oral and are interspersed between the sodium ascorbate and calcium administrations. This is accomplished by administering about 150 to about 300 mg Vitamin B1 on the off-hours between dosages of sodium ascorbate, calcium and mangesium. Administration of Vitamin B1 is on a p.r.n. basis according to observed need for inhibiting symptoms of neuritis. Generally, about one to about three grams Vitamin B1 given during the initial six hour period during detoxification is sufficient for controlling such symptoms.

To address vitamin B12 deficiencies, it is also presently preferred to administer about one to about three milligrams, during the initial six hours of detoxification, of a novel composition comprising a sublingual lozenge of Vitamin B12, in addition to the Vitamin B1 dosage.

This particular composition makes Vitamin B12 available immediately in the bloodstream via the sublingual artery, where it is optimally absorbed. The composition comprises selected concentrations of Vitamin B12, Vitamin E, Vitamin C, Vitamin B1, biotin and folic acid. The presently preferred concentrations of these components are as follows:

| Vitamin B12, | 1000 mcg. |
| Vitamin E, | 50 I.U. |
| Vitamin C, | 30 mg. |
| Vitamin B1, | 50 mg. |
| Biotin, | 150 mcg. |
| Folic Acid, | 100 mcg. |

Vitamins B1 and B12 have synergistic properties in regulating the autonomic nervous system. Vitamin E, Vitamin C and biotin enhance absorption of Vitamin B1 and B12 into the bloodstream.

Folic acid prevents undesirable depletion of folate from ingestion of excess Vitamin B12 over that absorbable by the body.

The composition is preferably formulated in lozenge form in any coventional pharmacological base which is capable of dissolving within about four minutes when held under the tongue. The lozenge is easily dissolvable, and the process takes about four minutes. Sublingual use makes the composition immediately available via the sublingual artery. As Vitamin B12 is inefficiently absorbed through the gastrointestinal tract, the sublingual lozenge has improved utility over more conventional Vitamin B12 tablets which are intended to be swallowed. Moreover, a sublingual lozenge provides patients a tool for helping themselves without resorting to a needle.

The above-described treatment accomplishes detoxification of the subject substantially without effects of withdrawal symptoms. As such, it has utility as an improvement over "cold turkey" methods or psychological counseling methods, or drug maintenance methods, such as substitution of Methodone for heroin. However, aside from addressing hypoascorbemia, and calcium, magnesium, phosphorous, and Vitamin B1 and B12 deficiencies, the described detoxification treatment does not purport to treat across-the-board nutritional deficiencies of the patient.

If such deficiencies, such as vitamin and mineral deficiencies, are present in the patient, and they often are due to the junk food "diet" of these patients, there is a substantial likelihood that, after detoxification, the patient will have a minimally functional mechanism for countering stress. Moreover, longterm ingestion of either drugs or alcohol may have destroyed or depleted whatever vitamins and minerals were in the patient's body to begin with. This is disadvantageous because normal stresses of everyday life can overload minimally functional stress mechanisms. Such a situation contributes to later reuse and experimentation with narcotic drugs in efforts to mask bodily nutritional deficiencies, or to combat stress. This method of this invention avoids these problems by addressing abuse of narcotizing substances as a largely metabolic problem. Therefore, while the previously described detoxification treatment has utility for accomplishing detoxification in the essential absence of withdrawal symptoms, I presently prefer that, after detoxification, nutritional deficiencies be addressed.

The essentials of the nutritional phase of the treatment will vary according to the toxic substances that was detoxified. Thus, the overall method, both in detoxification and its nutritional aspects, is treatment specific for offending substances and is tailored for meeting individual metabolic requirements. For this reason, prior to initiating treatment, the patient preferably is first given a series of metabolic tests and physical examinations for evaluating the patient's basic present metabolic profile, and the recent nutritional history of the patient.

These include a computerized medical history, a health hazard appraisal, a dietary evaluation, a complete blood count, VDRL, routine urinalysis, an SMA 23 blood chemistry, two chest and one flat abdomen x-rays, B12, folic acid level, serum amylase, T4, and a 24-hour urine quantitative amino acid fractionation, a psychological battery of tests, and analysis of a hair sample for trace and toxic metals. Results of these tests are combined for determining individual dietary needs. Beginning the day after detoxification, the patient is started on a diet tailored for rebuilding nutritional deficiencies.

The day after detoxification, the treatment enters a rebuilding phase characterized by a different treatment regimen. At this time, nutritional deficiencies are not masked by narcotic substances since detoxification has occurred. For this reason, symptoms of deficiency are at this time most acute and the deficiencies should preferably be addressed. Thus, administration of sodium ascorbate, calcium, magnesium and vitamins B1 and B12 are continued. During rehabilitation, which lasts until the end of the program, the daily dosage of sodium ascorbate, calcium, magnesium, and phosphorous is reduced compared with acute detoxification. In addition, the timing of the administration is changed to a basis which is preferably evenly divided three time a day, in place of the two hour repetitions, followed during detoxification.

During rehabilitation, administration of sodium ascorbate is reduced from the blocking dose level of about 28 to about 35 grams per day, to a daily dosage of about 6 about 8 grams, preferably given in one or two evenly divided dosages. Continued administration of sodium ascorbate is beneficial for building up the body's defense mechanisms. Calcium and magnesium are given in dosages of about 700 to about 800 milligrams, and about 250 to about 350 milligrams, respectively, for each divided dose of sodium ascorbate.

As bone meal is the preferred source of calcium, the administration of phosphorous is also similarly reduced, so that preferably phosphorous continues to be administered in a ratio of about one part phosphorous to about two to two and one half parts magnesium.

Sodium ascorbate, calcium and magnesium are discontinued for any day if and when the patient develops further diarrhea. At this point, the object is to rebuild nutritional deficiencies, and further diarrhea would be counterproductive.

Generally rehabilitation lasts about two weeks so that the entire treatment takes preferably 15 days to accomplish.

For the drug abuser, about 3 grams Vitamin B1 and one sublingual B12 lozenge containing about 1000 mcg Vitamin B12 are given daily, the Vitamin B1 being reduced after several days if neuritis symptoms no longer appear.

The day after detoxification, the patient is started on selected concentrations of zinc, pantothenic acid, and amino acids supplemented by selected concentrations of Vitamins A and B6.

Zinc is administered preferably in a dosage of about 60 to about 180 milligrams per day until normal appetite has returned to the patient. Generally, this process takes about four to five days. Although about 60 to about 180 milligrams are effective for inducing return of appetite, I prefer to administer about 180 milligrams zinc per day.

Upon return of appetite, zinc is reduced by a factor of about three, and is preferably continued on a daily basis of about 60 milligrams for the remainder of the treatment.

Pantothenic acid (Vitamin B5) provides support to the adrenal glands and is beneficial for preventing adrenal exhaustion. For these purposes, about 400 to about 1200 milligrams pantothenic acid is administered daily. I prefer to administer pantothenic acid in the form of 100 milligram tablets; on a basis of four tablets three times a day for a sufficient time until hypoglycemic swings disappear. Generally, this takes about four to five days.

The hypoglycemic swings are recognizable by those skilled in the art and are symptomatic of adrenal system imbalance. Disappearance of these symptoms indicate that the adrenal system is no longer in danger of exhaustion or severe depletion, and at that point, the dosage of pantothenic acid is preferably reduced to one 100 milligram tablet given three times daily for the remainder of the program.

A battery of amino acids is also initiated with zinc and pantothenic acid. The battery includes selected concentrations of 20 amino acids and is given on a basis of about 20 to 25 grams per day, preferably in divided dosages of about seven to eight grams per dose.

An important feature of the amino acid administration is that each amino acid is administered in the levulo or L form only, and not the D or D,L form. The levulo form of amino acids is immediately available for use in rebuilding the metabolism of the patient and for that reason, is presently preferred. While amino acids in either the D or D,L form could be used, they are not presently preferred because their utilization would require additional metabolic steps in digestion, absorption, and in the patient's liver. Hence, amino acids in the D or D,L forms would not be directly available to the patient and they are not as effective as amino acids in the levalo form. I presently prefer to administer an amino acid battery commercially available under the trademark ESSENAMINE TM and distributed by $M^2$ Ethical, Inc., of West Chicago, Ill.

Concurrent with the administration of the amino acid battery, are administered both vitamin A and vitamin B6. I prefer to administer about 5,000 to about 15,000 IU (International Units) vitamin A, preferably about 10,000 IU, and about 300 to about 800 milligrams Vitamin B6, preferably about 500 milligrams, each time a divided dosage of about seven to eight grams of the amino acids is given. The vitamin A and B6 are beneficial in aiding the liver to utilize amino acids in various metabolic cycles and enhance absorption of amino acids.

Administration of zinc, pantothenic acid, and the amino acids supplemented by vitamins A and B6, address three major metabolic problem areas in the detoxified patient. Zinc addresses gastrointestinal tract disorders arising from protracted intoxication and enhances the ability of the GI system to absorb nutrients and vitamins. The cumulative effect is that, once the patient has absorbed sufficient zinc, his body will be able to absorb essential nutrients when he eats.

Pantothenic acid, preferably supplemented by about 1 gram per day vitamin C in the form of ascorbic acid, provides relief to the adrenal system and repairs adrenal exhaustion, usually manifested as hypoglycemia. A healthy adrenal system provides the patient with adequate metabolic tools for handling stress.

The third component of the presently preferred nutritional treatment, the amino acids in levulo form, preferably supplemented by vitamins A and B6, reduce stress on the liver to aid proper conversion of partially digested substances into useful proteins directly utilizeable in metabolism. The amino acids increases the liver's usable supply of amino acids, and enables proper release of these proteins into the body for use in essential metabolic cycles.

Upon return of appetite, the zinc dosage is preferably reduced by a factor of about three, as previously described. The patient is then administered a mineral formula comprising selected concentrations of calcium, magnesium, iron, zinc, copper, iodine, molybdenum, chromium, selenium, and potassium. The presently preferred ranges of daily dosage levels of these minerals are as follows:

| Mineral | Range | Preferred |
| --- | --- | --- |
| Calcium | 1,000 to 1,500 mg. | 1350 mg. |
| Magnesium | 700 to 1,200 mg. | 1125 mg. |
| Iron | 30 to 80 mg. | 135 mg. |
| Zinc | 150 to 350 mg. | 225 mg. |
| Copper | 5 to 15 mg. | 9 mg. |
| Iodine | 0.30 to 0.80 mg. | 1.35 mg. |
| Manganese | 15 to 30 mg. | 22.5 mg. |
| Molybdenum | 0.3 to 1.0 mg. | 0.45 mg. |
| Chromium | 3 to 10 mg. | 4.5 mg. |
| Selenium | 0.05 to 0.20 mg. | 0.09 mg. |
| Potassium | 200 to 600 mg. | 450 mg. |

Generally the daily mineral formula described above, which is typical of these commercially available, is usually sufficient for correcting mineral deficiencies within about three to six months. However, if needed, additional supplementation of any of these minerals is performed by administering additional dosages of the required minerals to substantially correct the deficiency during the 6 month period after the patient has undergone treatment.

The patient is also given a multivitamin formula after appetite returns. This is preferably a formula which contains Vitamins A, D, the B complex, and E. Many suitable multivitamin formulas are commercially available. One such formula is marketed by Bronson, Inc. of West Covina, Calif., under the trademark BRONSON'S THERAPEUTIC FORMULA TM. Preferably two tablets of this formula are given after each meal.

Upon return of appetite, the patient is also given a daily regimen of B complex vitamin tablets, such as are commercially available which contains Vitamins B1, B2, B3, B5, B6, and B12. Such a complex addresses deficiencies of B-vitamins caused in part by a destructive influence of drugs or alcohol on the B complex, and in part by faulty diet.

Although these vitamins are needed for correcting deficiencies, the patient's stomach is not in a condition to accept them until appetite has returned. Thus, administration of B complex vitamins is delayed until the stomach is functioning normally.

The B complex vitamins are preferably given together as they function synergistically. The presently preferred daily dosage of B complex vitamins is about 200 to about 400 milligrams per day Vitamin B1, about 150 to 250 milligrams per day Vitamin B2, about 900 to about 1500 milligrams per day Vitamin B3, about 250 to about 500 milligrams per day Vitamin B5, about 150 to about 250 milligrams Vitamin B6, and about 2 to about 5 milligrams per day Vitamin B12. Of these, Vitamin B3 preferably is in the form of niacinamide, and vitamin B5 is in the form of calcium pantothenate.

As the B vitamins are water soluble, any excess of these vitamins given over what the body can absorb will be excreted through the urine and feces and for that reason is essentially harmless. Thus, it is preferable to administer the B-vitamin complex somewhat on the high side of the presently preferred ranges in order to fully address nutritional deficiencies without detriment to the patient. On the other hand, if a severe B vitamin deficiency problem is not addressed, due to a low dosage of B vitamins, neuritis and schizophrenic symptoms can be expected after appetite returns. The treatment is most beneficial to the patient, then, when the above described concentrations of Vitamins B1, sublingual B12 and B vitamin complex are administered, rapidly boosting the presence of these essential vitamins to normal levels. This has the additional benefit of providing the patient with adequate metabolic foods for handling stress.

The treatment is continued for about two weeks, with psychiatric testing and evaluation being performed initially, at 7 days, and at 14 days. The patient is counseled regarding proper nutrition tailored for individual metabolic needs and treated on an outpatient basis thereafter, with semiannual checkups during the first year to monitor metabolic progress.

The described nutritional treatment is presently preferred for treating patients dependant on or addicted to drugs and substances other than alcohol. For the alcoholic, the treatment program is slightly different in that additional substances are administered, in particular, lipotrates, digestive and pancreatic enzymes, N,N dimethylglycine, 1-glutamine, and lecithin. These address problem areas which are particularly troublesome to the alcoholic.

Detoxification for the alcoholic occurs rapidly after the initial diarrhea. Two problems later, excess loss of fluids and acute manifestation of Vitamin B-1 deficiency in the form of delerium tremens. The parentally-administered therapeutic detoxifying composition addresses these problems by supplying, in the form of the saline solution, adequate fluid compatible with the human body to prevent dehydration, and by providing thiamine hydrochloride (a form of Vitamin B-1) to counteract delerium tremens.

The alcoholic is also afflicted with malabsorption in the digestive tract, in particular the gastrointestinal tract. This generally manifests as severe protein depletion, and for this reason, the amino acids in the levulo form, preferably supplemented with Vitamin A and B6, are administered to address the problem immediately after detoxification.

Another affliction troublesome for alcoholics is liver dysfunction caused by fatty tissue infiltration. Such dysfunction causes Vitamin B12 to enter the circulatory system even though it is not needed. As a result, Vitamin B12 is cumulatively excreted and is severely depleted in alcoholics. This effect is more severe than with drug abusers and requires early attention. Hence three sublingual lozenges are given during detoxification of alcoholics with each divided dosage of sodium ascorbate.

The presence of elevated dosages of sodium ascorbate in the system during acute detoxification cooperates with Vitamin B12 in correcting liver dysfunction because sodium ascorbate has, in addition to its powers of detoxification and blocking withdrawal symptoms, beneficial powers for removing fatty tissue and serum cholesterol from the body. After detoxification, the alcoholic is given three sublingual B-12 lozenges daily until appetite returns, after which only one lozenge per day is given.

The alcoholic is usually afflicted with severe hypoglycemia, which generally manifests as exhaustion of the adrenal system. Therefore, pantothenic acid is administered to the alcoholic, in the same quantities as for the drug abuser, and cooperates with sodium ascorbate to correct adrenal dysfunction.

Due to special needs of the alcoholic, additional substances are administered to the alcoholic, but not the drug abuser, once detoxification has occurred. The alcoholic is administered a lipotropic formula for reducing tryglyceride levels in the bloodstream, a digestive and pancreatic enzyme formula, N,N dimethylglycine, a supplement of the amino acid glutamine in the levalo form, and a supplement of lecithin.

The lipotropic formula preferably comprises about 2500 mg. choline bitartrate, about 150 mg. betaine hydrochloride, about 15 mg. d-calcium pantothenate, and about 750 mg. lecithin, in a suitable pharmacological carrier. Any commercially available lipotropic formula containing these ingredients can be used. The lipotropic formula aids the body to break down fatty acids for reducing tryglyceride levels in the bloodstream. The presently preferred lipotropic formulation is commercially available under the trademark LIPOTRATE TM from M[2] Ethical, Inc., of West Chicago, Ill. Additional sufficient lecithin is also administered for increasing excretion of tryglycerides from the alcoholic patient. Generally, two tablespoons per day of lecithin are administered.

The amino acid L-glutamine is also administered in a preferred daily dosage of about 1 to about 3 grams, and preferably about 2 grams. L-glutamine is believed to have beneficial powers in absorption across a metabolic barrier associated with the brain cells. The beneficial absorption of glutamine can be enhanced by daily supplementation of about 600 milligrams magnesium ascorbate, and about 800 milligrams calcium ascorbate, with the preferred daily dosage of glutamine.

Also preferably given the alcoholic is an anti-oxidant, preferably a composition containing N,N dimethylglycine, after appetite returns. The anti-oxidant suppresses desire for alcohol. A commercially available form of this compound is marketed by DaVinci Laboratories, Inc. of So. Burlington, Vt. Preferably 3 or 4 tablets of this compound per day are given.

The usual treatment program preferably lasts about 15 days for all substances, whether the particular substance be alcohol or drug related. This period of time is sufficient for substantially correcting the metabolic health of the patient to where the patient has tools for handling stress and can function normally in society. At this point the patient exhibits a state of wellness characterized by essential absence of nutritionally induced metabolic deficiencies. The state of wellness substantially reduces the risk of returning to narcotizing substances.

The digestive and pancreatic enzymes are given in daily doses preferably in tablet form, and comprise:

| | |
|---|---|
| Glutamic acid HCl | 5 grains |
| Betaine HCl | 3 grains |
| Pepsin | 1 grain |
| Pancreatin enzyme Concentrate, enteric coated | 167 mg |
| Buse - Comfrey leaf | |

This formulation is commercially available from M[2] Ethical, Inc., West Chicago, Ill., under the trademark DIZYME TM. Preferably 2 or 3 tablets are given each day after meals. The pancreatic enzyme is enteric coated so that it is not absorbed until it reaches the small bowel. The other ingredients are digestive enzymes which aid return to normal digestive function.

The treatment can be administered either orally or intravenously or a combination of both. It is presently preferred that the treatment be entirely oral, with the exception of the therapeutic composition used during detoxification, which preferably is injected.

Once the patient has completed the initial 15-day treatment program, the patient has adequate levels of proteins and other essential nutrients in the body for functioning normally in society. However, individual patients have differing metabolic needs, and, after leaving the program, it is possible that, depending on individual metabolism, some of these levels may become cumulatively depleted. Therefore, when the patient completes the initial treatment program, the patient is again examined and counseled regarding individual metabolic needs and is prescribed vitamin and mineral supplements as are deemed necessary for maintaining a state of healthy metabolism. In general, each patient is placed on a holding dosage of about 6 to 10 grams sodium ascorbate per day, and whatever additional dosages appear necessary from analyzing the various physical assessments.

It is preferred that the patient return for periodic check-ups every six months for two years after the initial treatment program, and once each year thereafter.

Below are given summaries of two case histories of patients treated according to principles of this invention.

CASE HISTORIES

1. A thirty-one year old male with diagnosis of chronic alcoholism, severe, was admitted to the hospital at 1:00 p.m. He was immediately given 7 grams of sodium ascorbate in the powder form with two tablets of calcium with magnesium, containing calcium 375 mg and magnesium 150 mg per tablet. At hours two and four he was given 5 grams sodium ascorbate and two tablets of calcium with magnesium. Diarrhea began at 6:00 p.m. and again at 6:40 p.m. AT 8:15 p.m. patient began having muscle twitches and jerks. He also became nauseated and vomited.

An intravenous solution was at that time started with 500 cc of 0.9% normal saline which contained 500 mg of Vitamin B1 (thiamine hydrochloride), 400 mg magnesium chloride, and 400 mg calcium gluconate. At 10:30 p.m., 12.5 gms sodium ascorbate was added to the parenteral supply bottle, along with an additional 500 mg thiamine hydrochloride in 300 cc 0.9% normal saline. This was allowed to drip in over a four-hour period, at which time the patient was able to sleep and was considered detoxidifed.

The following day, he was stated on 7½ grams of amino acids four times daily with Vitamins A, B6, B1, B12, pantothenic acid, B complex and Vitamin E. These were combined with the minerals calcium and magnesium, potassium, iron, zinc, copper, iodine, manganese, molybdenum, chromium, selenium, betaine, HCl, citrus bioflavoid complex, and thymus, given several times daily for the purpose of restoring a norml healthy balance. This was continued daily through day 15, at which time the patient was discharged considered cured of alcoholism.

2. A 29-year old male was admitted to the hospital at 12:00 noon, with diagnosis of chronic polydrug abuse arising from daily ingestion of 12–16 grams codeine and 4–6 grams doriden for the past 5 years. He was immediately given 7 grams of sodium ascorbate in the powder form with two tablets of calcium with magnesium, containing 375 mg calcium and 150 mg magnesium per tablet. At hours two, four, and six he was given 5 grams sodium acorbate and two tablets of calcium and magnesium.

He was exhibiting no symptoms of withdrawal. At 7:00 he was given a parenteral dose of 1000 cc 0.9% normal saline solution containing 60 cc (15 grams) sodium ascorbate, 5 cc thiamine hydrochloride (500 mg), 2 cc magnesium chloride containing 400 mg magnesium as MgCl, and 2 cc calcium gluconate (1.6 milliequivalents calcium). The solution was allowed to drip in over a four-hour period. At 9:15 the patient fell asleep and slept until the following morning with no sign of withdrawal. He was considered detoxified at the end of the IV since he slept peacefully and had no "guts craving" for the drugs the second morning, and even showered.

The second day he entered the standard daily program (as per case 1) of amino acids, vitamins, minerals and other supplements for rebuilding nutritional health, and at this writing, is progressing normally.

I claim:

1. In a method for detoxifying a patient from an alcohol or drug dependence, wherein the patient is caused to discontinue further ingestion of alcohol or the dependency-inducing drug, thereby to induce the patient to undergo withdrawal from alcohol or the dependency-inducing drug, until the patient is detoxified,
an improved method for detoxifying such a patient, where, upon causing the patient to discontinue further ingestion of alcohol or the dependency-inducing drug, the improved method comprises:
administering at least about 30 grams sodium ascorbate to the patient thereby to detoxify the patient, by:
orally giving a portion of the sodium ascorbate to the patient, and
intravenously infusing the remainder of the sodium ascorbate into the patient; and
intravenously infusing sufficient fluid into the patient with the infusing sodium ascorbate to prevent dehydration.

2. A method according to claim 1 wherein the fluid comprises, per 1000 ml volume:
from about 10 g to about 15 g sodium ascorbate;
from about 400 mg to about 800 mg calcium gluconate;
from about 200 mg to about 400 mg magnesium chloride; and
from about 500 mg to about 1000 mg thiamine hydrochloride.

3. A method according to claim 2 further comprising: controlling the rate of infusion of the fluid into the patient as needed for limiting symptoms of withdrawal from alcohol or the dependency-inducing drug.

4. A method according to claim 3 wherein at least about 1000 ml of such fluid is infused into the patient within from about 2 hours to about 4 hours after starting such intravenous infusion of fluid.

5. A method according to claim 1 wherein the oral portion of the sodium ascorbate is given in divided doses of from about 4 g to about 8 g every 2 hours for 6 hours, or until the patient experiences diarrhea, whichever occurs first.

6. A method according to claim 5 further comprising giving, orally, per each divided dose of orally-given sodium ascorbate:
from about 600 mg to about 800 mg calcium,
from about 250 mg to about 350 mg magnesium, and
from about 113 mg to about 250 mg phosphorus.

7. In a method for detoxifiying a patient from an alcohol or drum dependence, whereby such method consists of preventing further ingestion of alcohol or drugs until the patient is considered detoxified,
an improved method for detoxifying the patient, where, upon preventing the patient from further ingesting alcohol or drugs, the improved method comprises:
orally administering, every 2 hours for up to 6 hours, or until the patient experiences diarrhea, whichever occurs first:
from about 4 g to about 8 g sodium ascorbate;
from about 600 mg to about 800 mg calcium; and
from about 250 mg to about 350 mg magnesium;
accelerating the process of detoxification by intravenously infusing at least about 1000 ml of a fluid comprising, per 1000 ml of fluid:
from about 10 g to about 15 g sodium ascorbate,
from about 400 mg to about 800 mg calcium gluconate,
from about 200 mg to about 400 mg magnesium chloride, and
from about 500 mg to about 1000 mg thiamine hydrochloride; and
increasing the rate of infusion of the fluid into the patient as needed for limiting withdrawal symptoms.

8. A method according to claim 7 wherein the fluid is completely infused within about 2 hours to about 4 hours after starting such intravenous infusion of fluid.

9. In a method for detoxifying a patient from an alcohol or drug dependence, wherein such method consists of causing the patient to discontinue ingesting alcohol or drugs until the patient is considered detoxified,
an improved method for detoxifying the patient, where, upon causing the patient to discontinue ingesting alcohol or drugs, the improved method comprises:
orally administering, every 2 hours for up to 6 hours, or until the patient experiences diarrhea, whichever occurs first:
about 4 g to about 6 g sodium ascorbate;
about 600 mg to about 800 mg calcium; and
about 250 mg to about 350 mg magnesium;
intravenously supplying sufficient fluid to the patient to prevent dehydration, by infusing at least about 1000 ml of a solution comprising, per 1000 ml:
about 10 g to about 15 g sodium ascorbate;
about 400 mg to about 800 mg calcium gluconate, about 200 mg to about 400 mg magnesium chloride, and about 500 mg to about 1000 mg thiamine hydrochloride; and controlling the rate of infusion of the solution as needed to limit objective withdrawal symptoms until the patient is detoxified.

10. A method for detoxifying a patient from an alcohol dependence, the method comprising:

denying the patient further ingestion of alcohol;

orally administering, once every 2 hours for up to six hours, or until the patient experiences diarrhea, whichever occurs first:

from about 4 g to about 8 g sodium ascorbate, from about 600 mg to about 800 mg calcium, and from about 250 mg to about 350 mg magnesium;

intravenously infusing at least about 1000 ml of a solution thereby to prevent dehydration, the solution being compatible with blood serum and comprising, per 1000 ml:

from about 10 g to about 15 g sodium ascorbate, from about 400 mg to about 800 mg calcium gluconate, from about 200 mg to about 400 mg magnesium chloride, and from about 500 mg to about 1000 mg thiamine hydrochloride; and increasing the rate of infusion of the solution into the patient as needed to control delerium tremens until the patient is detoxified.

11. A method according to claim 10 further comprising orally administering, concurrently with each oral dose of calcium, from about 113 mg to about 250 mg phosphorus.

12. A method for detoxifying a person from an alcohol or drug dependence comprising intravenously infusing an effective amount of a composition comprising the following per 1000 ml: from about 10 g to about 15 g sodium ascorbate, from about 400 mg to about 800 mg calcium gluconate, from about 200 mg to about 400 mg magnesium chloride, and from about 500 mg to about 1000 mg thiamine hydrochloride to detoxity the person in the essential absence of withdrawal symptoms.

13. A method for detoxifying a person from an alcohol or drug dependence comprising intravenously infusing an effective amount of a composition for limiting withdrawal symptoms during detoxification from such alcohol or drug dependence, the composition comprising the following per 1000 ml:

from about 10 g to about 15 g sodium ascorbate, from about 400 mg to about 800 mg calcium gluconate, from about 200 mg to about 400 mg magnesium chloride, and from about 500 mg to about 1000 mg thiamine hydrochloride.

* * * * *